(12) United States Patent
Masuyama et al.

(10) Patent No.: US 6,410,685 B1
(45) Date of Patent: Jun. 25, 2002

(54) ANTISTRESS AGENTS AND FUNCTIONAL FOODS

(75) Inventors: Akihiro Masuyama, Yokohama; Toshiaki Takano, Kawasaki, both of (JP)

(73) Assignee: Calpis Co., Ltd., Tokyo (JP)

( * ) Notice: Subject to any disclaimer, the term of this patent is extended or adjusted under 35 U.S.C. 154(b) by 0 days.

(21) Appl. No.: 09/508,777

(22) PCT Filed: Feb. 5, 1998

(86) PCT No.: PCT/JP98/00480

§ 371 (c)(1), (2), (4) Date: Mar. 15, 2000

(87) PCT Pub. No.: WO99/16461

PCT Pub. Date: Apr. 8, 1999

(30) Foreign Application Priority Data

Sep. 26, 1997 (JP) .............................................. 9-262422

(51) Int. Cl.$^7$ ................................................. C07K 5/08
(52) U.S. Cl. ......................................... 530/331; 514/18
(58) Field of Search ............................. 514/8; 530/331; 424/439

(56) References Cited

U.S. PATENT DOCUMENTS 5,574,013 A * 11/1996 Horwell .......................... 514/18
5,639,729 A * 6/1997 Goldstein ....................... 514/18
5,846,942 A * 12/1998 Horwell .......................... 514/18

OTHER PUBLICATIONS

Iwao Kuwajima, et al., Effect of Perindopril on 24–Hour Blood Pressure Levels and Hemodynamic Responses to Physical and Mental Stress in Elderly Hypertensive Patients, Clinical Therapeutics, vol. 16, No. 6, 962–972 (1994).

J.A. Oben, et a., The Stimulation of IL–2 Production by Anti–Rheumatic Drugs, Immunology 67, 328–332 (1989).

Jeffrey R. Hazelette, et al., A 52–Week Oral Chronic Toxicity Study on CGS 14824 A in Rats, Basic Pharmacology & Therapeutics (Yakuri to Chiryo), vol. 19, No. 10, pp. 3863–3891 (1991).

Makoto Saitoh, et al. , Effects of an Angiotensin–Converting Enzyme Inhibitor, Alacepril on Cardiovascular and Sympathetic Nervous Responses to Mental Stress in Patients with Essential Hypertension, Internal Medicine, vol. 32, No. 9 (Sep. 1993).

Osamu Masuda, et al., Antihypertensive Peptides are Present in Aorta After Oral Administration of Sour Milk Containing These Peptides to Spontaneously Hypertensive Rats, American Institute of Nutrition, vol. 126, No. 12 (1996) p. 3063–3068.

Yasunori Nakamura, et al., Antihypertensive Effect of Sour Milk and Peptides Isolated from it that are Inhibitors to Angiotensin I–Converting Enzyme, J. Dairy Sci., vol. 78, No. 6 (1995) p. 1253–1257.

\* cited by examiner

*Primary Examiner*—Christopher S. F. Low
*Assistant Examiner*—David Lukton
(74) *Attorney, Agent, or Firm*—Darby & Darby

(57) ABSTRACT

The invention provides a method for reducing stress comprising administering an anti-stress agent winch can be administered repeatedly and daily without any problems with safety, and which can mitigate and prevent mental and physical symptoms cause by stress. The anti-stress gent comprises as an effective ingredient a tripeptide, particularly Ile-Pro-Pro and/or Val-Pro-Pro and/or a salt thereof, having angiotensin converting enzyme inhibitory activity.

1 Claim, No Drawings

ANTISTRESS AGENTS AND FUNCTIONAL FOODS

FIELD OF ART

This invention relates to an anti-stress agent and functional food having effects of preventing and mitigating mental and physical symptoms caused by stress.

BACKGROUND ART

In the modern society, people undergoes various kinds of stress caused by highly advanced and complicated scientific technology, or drastically changing social circumstances. Particularly, in the internationalized society, complex human relationships are formed, causing mental stress. It has been reported that a variety of symptoms are caused by mental stress.

It is recognized that mental stress has a great influence on circulatory system and immune system. However, the scientific concept and definition of stress have not yet been well established, so that means of evaluation of stress still have many problems, combined with methodological difficulties. However, in the recent years, studies of stress have been made from the medical point of view.

For example, it is reported that when one undergoes stress, angiotensin II increases, and intracorporeal sodium due to sodium reabsorbancy becomes excess, which causes rise in blood pressure (Osamu Mobara et al.: Taisha, 28, 2, 323, 1991). Based on such findings, studies have been made on the effect of enalapril and alacepril, which are angiotensin converting enzyme inhibitors and used as antihypertensive agents, on hypertension caused by stress (The American Journal of Cardiology; 68, 15, 1362(1991), Internal Medicine; 32, 9, 691(1993)). However, it is considered that suffering stress not only causes rise in blood pressure, but also influences various factors to cause stomach ulcer, ischemic heart diseases, cerebrovascular diseases, hyperlipemia, or the like. Therefore, though stress is regarded as one of the causes of hypertension, it is not believed that the anti-stress effect is achieved merely by suppressing the rise in blood pressure.

As an agent for preventing and mitigating mental and physical symptoms caused by stress, chemically synthesized medicaments such as a tranquilizer, an antianxiety agent, and sleeping pills are presently used. However, these medicaments have habituation and side effect problems, so that it is not preferable to use them daily for the purpose of preventing mental and physical symptoms caused by stress. Accordingly, an anti-stress agent that can be taken repeatedly and daily without any problems with safety, and that can mitigate and prevent mental and physical symptoms caused by stress are desired and are under development. For example, there are proposals such as an anti-stress agent containing as an effective ingredient L-theanine contained in tea leaves (Japanese Laid-open Patent Application No. 6-100442), an anti-stress composition containing imidazole compounds such as anserine, valenine, n-methylhistidine, or r-methylhistidine (Japanese Laid-open Patent Application No. 9-20660), and anti-stress food containing a composition of glutathione and antioxidant (Japanese Laid-open Patent Application No. 8-275752). There is also a report on stress reducing effect of fragrance (Fragrance Journal: 1991–11, p44–49). However, there has not been reported that a tripeptide has the effect of mitigating and preventing mental and physical symptoms caused by stress.

DISCLOSURE OF THE INVENTION

It is an object of the present invention to provide an anti-stress agent and functional food which can fulfill the social demand as mentioned above, which can be taken repeatedly and daily without any problems with safety, and which can mitigate and prevent mental and physical symptoms caused by stress.

According to the present invention, there is provided an anti-stress agent comprising as an effective ingredient a tripeptide and/or a salt thereof having angiotensin converting enzyme inhibitory activity.

According to the present invention, there is also provided the anti-stress agent wherein said tripeptide is Ile-Pro-Pro and/or Val-Pro-Pro.

According to the present invention, there is further provided use of the tripeptide and/or the salt thereof for the manufacture of an anti-stress agent.

According to the present invention, there is also provided food having an anti-stress effect and comprising said anti-stress agent.

According to the present invention, there is further provided use of the tripeptide and/or the salt thereof for the manufacture of food having an anti-stress effect.

According to the present invention, there is further provided a method for producing the food having anti-stress effect comprising fermenting a medium containing a peptide and/or a protein including a sequence Ile-Pro-Pro and/or Val-Pro-Pro with lactic acid bacteria under conditions for a tripeptide Ile-Pro-Pro and/or Val-Pro-Pro to be produced in a resulting fermented medium.

According to the present invention, there is also provided a method for reducing stress comprising orally administering an effective amount of a tripeptide and/or a salt thereof having angiotensin-converting enzyme inhibitory activity.

PREFERRED EMBODIMENTS OF THE INVENTION

The anti-stress agent of the present invention contains, as an effective ingredient, a tripeptide and/or a salt thereof having angiotensin converting enzyme inhibitory activity. In the present invention, "anti-stress" effect means an activity to cause approximation of the conditions of a subject to the conditions without stress, e.g., an activity to reduce systolic and diastolic blood pressures which have been increased due to stress, and an activity to inhibit or prevent lowering in immunological function caused by stress, such as lowering in spleen cell response.

The tripeptide may be preferably selected from the group consisting of Ile-Pro-Pro, Val-Pro-Pro (abbreviated hereinbelow as IPP and VPP, respectively) and mixtures thereof that have angiotensin converting enzyme inhibitory activity.

The salt of the tripeptide may include pharmacologically acceptable salts, such as inorganic salts such as hydrochloride, sulfate and phosphate, and organic salts such as citrate, maleate, fumarate, tartrate and lactate.

The tripeptide may be produced by, e.g., fermentation with microorganism, enzyme hydrolysis, or chemical synthesis.

The fermentation with microorganism can be performed by culturing lactic acid bacteria in a medium of a food material containing a peptide and/or a protein including an amino acid sequence corresponding to the tripeptide, such as sequences Ile-Pro-Pro and/or Val-Pro-Pro.

The medium is preferably a food material containing a peptide and/or a protein including an amino acid sequence corresponding to the tripeptides. The food material may be milk, milk casein, corn, corn protein, wheat, wheat protein, soybean, de-fat soybean or soybean protein. The medium may further contain other ingredients such as yeast extract, vitamins and minerals, if necessary.

As the lactic acid bacteria, lactic acid bacteria of the genus Lactobacillus may be employed. For example, *Lactobacillus helveticus, Lactobacillus delbruekii* subsp. *bulgaricus, Lactobacillus acidophilus, Lactobacillus fermentum* or *Lactobacillus casei* subsp. *casei* maybe employed. Specifically, *Lactobacillus helveticus* ATCC55796, *Lactobacillus delbruekii* subsp. *bulgaricus* ATCC11842, *Lactobacillus acidophilus* ATCC4356, *Lactobacillus fermentum* ATCC14931 or *Lactobacillus casei* subsp. *casei* ATCC393 may be employed.

The fermentation may be performed by heat-sterilizing the medium, cooling the medium to a desired culturing temperature, and then inoculating the medium with a pre-cultured lactic acid bacteria starter. The inoculation amount of the lactic acid bacteria starter is preferably $10^5$ to $10^7$ cells of the lactic acid bacteria per 1 g of the medium. The culture temperature may be 20 to 50° C., and preferably 30 to 45° C. The culturing time maybe 3 to 48 hours, and preferably 6 to 24 hours. The culturing may be terminated when number of cells of the lactic acid bacteria reaches $10^8$ cells/g or more and acidity of the lactic acid reaches 1 or more. The resulting cultured medium usually contains 0.1 to 100 μg/g of IPP and/or VPP, although it depends on the material and composition of the medium.

The cultured medium itself containing live lactic acid bacteria may be used as the anti-stress agent of the present invention. Alternatively, the cultured medium may be used after heat-sterilizing, e.g., up to 80° C. Further, the cultured medium may be used after being powdered by freeze drying, spray drying or drum dryer drying.

The cultured medium may be concentrated to purify the tripeptide before use as the anti-stress agent of the present invention. The concentration and purification may be carried out by subjecting the cultured medium to centrifugation and taking supernatant of the centrifuged liquid. The supernatant may further be subjected to electrodialysis, ion exchange resin treatment, hollow fiber membrane dialysis, reverse osmosis treatment, hydrophobic column chromatography, or combinations thereof, to obtain a further concentrated and purified tripeptide.

The enzyme hydrolysis for producing the tripeptide may include treating a food material containing a peptide and/or a protein including an amino acid sequence corresponding to the tripeptides such as Ile-Pro-Pro and Val-Pro-Pro, successively with proteinase and carboxypeptidase. The proteinase may be proteinase derived from microorganisms, from plants, or from animals, and may be prepared by a publicly known method. The carboxypeptidase may be carboxypeptidase derived from microorganisms, from plants, or from animals, and may be prepared by a publicly known method.

The chemical synthesis for producing the tripeptide may include publicly known organic synthesis. For example, the tripeptide may be obtained by preparing amino acids that are components of the objective tripeptide, protecting the amino group of each amino acid with a fluorenylmethoxycarbonyl group, successively reacting the amino acids protected with the fluorenylmethoxycarbonyl group in accordance with the amino acid sequence of the objective tripeptide by any conventional method, to obtain a tripeptide bound to a resin, and then removing the resin by any conventional method and purifying the tripeptide.

The content of the tripeptide in the anti-stress agent of the present invention is not particularly limited as long as it enables administration of the effective amount of the tripeptide to be discussed later. The content of the tripeptide may usually be 0.001 to 1 wt % of the agent.

The anti-stress agent of the present invention may contain, in addition to the tripeptide and/or the salt thereof, other additives such as sugars, proteins, lipids, vitamins, minerals, flavoring agents and coloring agents.

The anti-stress agent of the present invention may be administered to humans or animals. The administration may be performed orally or intravenously, with the oral administration being preferable.

Effective administration amount of the anti-stress agent of the present invention may usually be, for example, in a range of 0.1 to 40 mg/kg body weight·day in terms of the tripeptide for oral administration, in order to achieve the effect of the present invention such as mitigation and prevention of stress in human. However, the anti-stress agent may be administered in an amount exceeding this range.

When the anti-stress agent of the present invention is administered to a subject, changes in various physiological indices in response to stress, such as rise in blood pressure, lowering in immunological functions, becomes smaller than that in a case in which the present agent is not administered, and approximates to that in a case in which stress is not loaded.

The functional food of the present invention contains the anti-stress agent. Taking this functional food prevents or mitigates the stress.

The content of the anti-stress agent in the functional food of the present invention is not particularly limited as long as it is in a range to enable the tripeptide and/or the salt thereof in the functional food achieves the anti-stress effect. The functional food may usually contain the anti-stress agent in an amount to make the content of the tripeptide and/or the salt thereof in the functional food be 0.001 to 0.1 wt %.

By taking the functional food of the present invention in an amount ranging from 0.1 to 40 mg in terms of the tripeptide per kg body weight·day, preferable effects of the present invention may be obtained. However, the functional food may be taken in an amount exceeding this range.

The functional food of the present invention may include yogurt, milk-containing acidified beverages, cheese, processed foods and beverages containing fermented sour milk or health foods, and may be in the form of solid such as powders, granules and tablets, or of fluid such as paste, gel and liquid.

The tripeptide, the effective ingredient of the anti-stress agent and the functional food of the present invention may be obtained by fermenting a food material with lactic acid bacteria, and thus is quite safe.

Since the anti-stress agent and the functional food of the present invention contain the tripeptide, they are quite safe, and repeated and daily intake thereof can mitigate and prevent mental and physical symptoms caused by various kinds of stress.

EXAMPLES OF THE INVENTION

The present invention will be explained more in detail referring to the Examples, but the present invention is not limited thereto.

Example 1

9 g of skim milk powders were dissolved in 100 g of water. The resulting solution was sterilized at 115° C. for 20 minutes, cooled to room temperature, inoculated with 1 platinum loop of *Lactobacillus helveticus* ATCC-8205, and cultured at 37° C. for 24 hours, to prepare a primary starter ($5 \times 10^8$ cells/ml, pH 3.5). Subsequently, 2 kg of skim milk (containing 9 wt % solids) sterilized by heating up to 90° C. was inoculated with 80 g of the primary starter, and cultured at 37° C. for 24 hours, to prepare a secondary starter. Then, 4.5 kg of skim milk powders were dissolved in 50 kg of water. The resulting solution was sterilized by heating up to 90° C., cooled to room temperature, inoculated with 2 kg of the secondary starter, and cultured at 37° C. for 24 hours, to obtain 56 kg of fermented milk. The content of IPP and VPP in the fermented milk thus obtained was 5.4 mg and 9.5 mg per litter, respectively.

Example 2

6 kg of the fermented milk prepared in Example 1 was adjusted to pH 7.3 with 10N aqueous solution of sodium hydroxide, admixed with one liter of an ion exchange resin (trade name "Amberlite XAD-2" manufactured by ORGANO CORP.), and further admixed with distilled water so that the total weight of the resulting mixture was 20 kg. The mixture was stirred with a stirrer for 90 minutes, and filtrated with a suction filtration device to separate the resin. The resin on the filter was washed with 20 kg of distilled water, and then the washed resin was collected. The collected resin was admixed with 0.8 kg of methanol, and stirred for 30 minutes with a stirrer. The resulting mixture was filtrated through nylon wool (200 mesh) and then through a hard filter paper by suction. The obtained filtrate was concentrated under a reduced pressure at 55° C. with an evaporator, to obtain 200 g of concentrated liquid. The liquid was admixed with 250 ml of an ion exchange resin (trade name "Amberlite IRA-400 (OH type)", manufactured by ORGANO CORP.), stirred for 10 minutes, and filtrated through a filter paper by suction. The filtrate was adjusted to pH 7 with 1N hydrochloric acid solution, and freeze dried. The product thus purified and dried was uniformly dissolved in 5 ml of distilled water, applied to a column (trade name "Sephadex G-25" manufactured by PHARMACIA CO.), and eluted with distilled water, to collect a tripeptide fraction. The fraction was freeze dried to obtain 50 mg of powders of the purified tripeptide fraction. 50 mg of the powders of the purified tripeptide fraction contained 0.6 mg of IPP and 1.0 mg of VPP.

Example 3

IPP and VPP were synthesized by the following organic chemistry synthesis. The synthesis was performed in accordance with solid phase method using automatic peptide synthesis apparatus (Type PSSM-8) manufactured by SHIMADZU CO. As a solid phase carrier, 20 μmol of a polystyrene resin of benzyloxybenzyl alcohol type to which proline having an amino group protected with a fluorenyl-methoxycarbonyl group (referred to hereinbelow as Fmoc) was bound was employed. In accordance with the amino acid sequence, Fmoc-Ile, Fmoc-Pro and Fmoc-Val each having an amino group protected with the Fmoc group were successively reacted by 100 μmol each by a conventional method, to obtain a peptide-bound resin. The peptide-bound resin was suspended in 1 ml of a reaction liquid (containing 1 wt % ethanedithiol, 5 wt % anisole and 94 wt % trifluoroacetic acid) and reacted for 2 hours at room temperature to separate the peptides from the resin and to remove the side chain protecting group from the peptides. The reaction mixture was filtrated through a glass filter, admixed with 10 ml of anhydrous ether to precipitate the purified peptide, and centrifuged at 3000 rpm for 5 minutes to separate the precipitate. The precipitate was washed with anhydrous ether several times, and dried by blowing nitrogen gas. All the crude synthesized peptides thus obtained was dissolved in 2 ml of 0.1N hydrochloric acid aqueous solution, and then purified by HPLC on a reverse phase column of $C_{18}$ in accordance with the following conditions:

Pump: Type L6200 intelligent pump (HITACHI, LTD.)

Detector: Type L4000 UV detector (HITACHI, LTD.) for detecting UV absorbance at 215 nm Column: MICROBONDASPHERE 5 μ$C_{18}$ (manufactured by WATERS INC.)

Eluent: liquid A; 0.1 wt % TFA aqueous solution liquid B; acetonitrile containing 0.1 wt % TFA (B/A+B)×100(%): 0→40% (60 minutes)

Flow rate: 1 ml/min.

Eluate fraction at the maximum absorbance were collected and freeze dried to obtain the objective synthesized peptides, i.e., 2.1 g of IPP and 0.9 mg of VPP. The purified peptides were analyzed from their N-terminus with a full automatic protein primary structure analyzer (Type PPSQ-10 manufactured by SHIMADZU CO.), and with an amino acid analyzer (Type 800 series, manufactured by NIHON BUNKOU KOUGYO CO.). As a result, these peptides were found to be as designed.

Example 4

24 male Wister rats (body weight about 300 g) were preliminarily fed for one week. During the preliminary feeding period and the experimental period, the rats were restrictively fed with commercial diet (trade name "CE-2" manufactured by NIHON CREA CO.), and allowed to take water ad libitum.

After the preliminary feeding period, the rats were divided into three groups (eight rats each), namely, (1) the group not exposed to stress and given saline, (2) the group exposed to stress and given saline, and (3) the group exposed to stress, and given VPP and IPP. The animals of groups (2) and (3) were exposed to stress for 9 days by putting them in a cold room (4° C.) for 4 hours per one day.

On the day 10, rats of groups (1) and (2) were given 1 ml of saline, and rats of group (3) were given 1 ml of saline containing 3 mg/kg body weight each of IPP and VPP synthesized in Example 3, by forcible administration into stomach via an oral sonde. After the administration, the rats of groups (2) and (3) were exposed to cold stress for 4 hours. Two hours after finishing the stress loading, blood pressure of the rats in each group was measured by tail-cuff method using a non-warming, non-invasive rat sphygmomanometer (Type PE-300, manufactured by CSI CO.). The results are shown in Table 1.

The results of blood pressure are shown in Table 1. As shown in Table 1, both systolic and diastolic blood pressures were higher in group (2) which were exposed to stress than in group (1) which were not exposed to stress. On the contrary, both systolic and diastolic blood pressures of group (3) rats which received VPP and IPP were lower than those of group (2) rats which received saline, and approximated to those of group (1) rats which were not exposed to stress.

TABLE 1

| Experimental Groups | Systolic Blood Pressure (mmHg) | Diastolic Blood Pressure (mmHg) |
| --- | --- | --- |
| (1) no-stress, given saline | 121 | 97 |
| (2) stressed, given saline | 136* | 107 |
| (3) stressed, given VPP and IPP | 129 | 101 |

*significantly different from group (1) with significance level of 5%

Changes in blood pressure before and after the cold stress are shown in Table 2. As shown in Table 2, both systolic and diastolic blood pressures were increased significantly in group (2) which were exposed to stress, compared to group (1) which were not exposed to stress. Increase in both systolic and diastolic blood pressures were suppressed in group (3) which received VPP and IPP, compared to group (2) which received saline. Particularly, suppression of increase in systolic blood pressure was significant. From these results, it was confirmed that administration of IPP and VPP results in suppression of increase in blood pressure induced by stress.

TABLE 2

| Experimental Groups | Systolic Blood Pressure (ΔmmHg) | Diastolic Blood Pressure (ΔmmHg) |
| --- | --- | --- |
| (1) no-stress, given saline | −2.2 | −2.5 |
| (2) stressed, given saline | 11.2* | 6.1* |
| (3) stressed, givenvPPandIPP | 3.7# | −0.6 |

*significantly different from group (1) with significance level of 5%
significantly different from group (2) with significance level of 5%

Example 5

24 male Wister rats (body weight about 300 g) were preliminarily fed for one week. During the preliminary feeding period and the experimental period, the rats were restrictively fed with commercial diet (trade name "CE-2" manufactured by NIHON CREA CO.), and allowed to take water ad libitum.

After the preliminary feeding period, the rats were divided into three groups (eight rats each), namely, (1) the group given saline, (2) the group given VPP, and (3) the group given IPP. The rats of groups (1) to (3) were exposed to stress for 9 days by, as in Example 4, putting them in a cold room (4° C.) for 4 hours per one day.

On the day 10, rats of group (1) were given 1 ml of saline, and rats of group (2) and (3) were given 1 ml of saline containing 3 mg/kg body weight of IPP or 3 mg/kg body weight of VPP, respectively, synthesized in Example 3, by forcible administration into stomach via an oral sonde. After the administration, the rats of groups (1) to (3) were exposed to cold stress for 4 hours, and blood pressure was measured as in Example 4. The results are shown in Table 3.

The results of blood pressure are shown in Table 3. As shown in Table 3, both systolic and diastolic blood pressures were significantly lower in groups (2) and (3) which received tripeptides than in group (1) which received saline. It was recognized that administration of the tripeptides results in suppression of increase in blood pressure induced by stress.

TABLE 3

| Experimental Groups | Systolic Blood Pressure (mmHg) | Diastolic Blood Pressure (mmHg) |
| --- | --- | --- |
| (1) saline | 138 | 110 |
| (2) VPP administration | 131* | 101* |
| (3) IPP administration | 130* | 102* |

*significantly different from group (1) with significance level of 5%

Example 6

The test was carried out in the same way as in Example 5 except that the group (1) rats were given 2 ml of saline, and the rats in group (2) were given 5 ml/kg body weight of the fermented milk obtained in Example 1, and the rats in group (3) were given 2 ml of saline containing 150 mg/kg of the purified tripeptide fraction powders obtained in Example 2, respectively. After the administration of the samples and exposure to stress, the blood pressure of each rat was measured.

The results of blood pressure are shown in Table 4. As shown in Table 4, comparing group (2) which received the fermented milk and group (3) which received the purified tripeptide fraction powders with group (1) which received saline, both systolic and diastolic blood pressures were lower in groups (2) and (3) than in group (1). It was thus recognized that administration of the fermented milk and the purified tripeptide fraction results in suppression of increase in blood pressure induced by stress.

TABLE 4

| Experimental Groups | Systolic Blood Pressure (mmHg) | Diastolic Blood Pressure (mmHg) |
| --- | --- | --- |
| (1) saline | 135 | 106 |
| (2) fermented milk | 132 | 99* |
| (3) purified tripeptide fraction | 128* | 101* | significantly different from group (1) with significance level of 5%

Example 7

24 male Wister rats (body weight about 300 g) were preliminarily fed for one week. During the preliminary feeding period, the rats were restrictively fed with commercial diet (trade name "CE-2" manufactured by NIHON CREA CO.), and allowed to take water ad libitum.

After the preliminary feeding period, the rats were divided into three groups (eight rats each), namely, (1) the group not exposed to stress and given saline, (2) the group exposed to stress and given saline, and (3) the group exposed to stress, and given VPP and IPP. The animals of groups (2) and (3) were exposed to water immersion restraint stress for 6 hours per one day for consecutive 5 days by putting the animals in a wire cage for restraint and immersing them in a water bath at 25° C. with their heads above the water surface for breathing. During the stress loading period, the rats were allowed to take commercial diet (trade name "CE-2" manufactured by NIHON CREA CO.) and water ad libitum.

The rats were given samples throughout the consecutive 5 days of stress. As the samples, 1 ml of saline was given to groups (1) and (2), and 1 ml of saline containing 3 mg/kg body weight each of IPP and VPP synthesized in Example 3 to group (3), by forcible administration into stomach via an oral sonde.

From the second day to the third day of stress loading, urine was collected using a metabolic cage, and analyzed with HPLC to measure the levels of catecholamine and indoleamine. A silica reverse phase column (trade name "Catecholpack") manufactured by NIHON BUNKOU KOUGYO CO. and an electrochemical detector (trade name "Coulochem") manufactured by esa CO. were employed in the analysis.

After the exposure to stress was finished on the final day of loading stress, the rats were sacrificed by decapitation, to collect blood and take out thymus and spleen. Amino acid composition of the serum was measured by amino acid analyzer (Type 800 series, manufactured by NIHON BUNKOU KOGYO CO.), to calculate Fischer ratio (molar ratio of branched chain amino acid /aromatic amino acid). The weight of thymus and lever was measured. Spleen cells were prepared from spleen and measured for interleukin 2 productivity and mitogen reactivity in accordance with the following procedure.

(Preparation of Spleen Cells)

Spleen was finely ground in a homogenizer, subjected to hypotonic treatment to remove hemocyte, washed with MEM containing 2% fetal calf serum (FCS), and suspended in RPM 1640 medium containing 10% FCS, to prepare a free cell suspension containing $1 \times 10^7$ cells.

(Measurement of Interleukin 2 Productivity)

RPM 1640 medium containing $2.5 \times 10^6$ cells of the spleen cells prepared above, 5 μg/ml of concanavalin A (ConA) and 10% FCS was prepared, and cultured for 24 hours. The amount of interleukin 2 in the supernatant of the cultured medium was measured by bioassay using as an index proliferation of an interleukin 2 reactive cell strain.

(Mitogen Reactivity)

RPM 1640 medium containing 5 μg/ml of either ConA or a pokeweed mitogen (PWM) as a mitogen, $5 \times 10^6$ cells of the spleen cells prepared above and 10% FCS was prepared, and cultured for 24 hours. The number of the cells after 24 hours was measured by absorbance, using intake of MTT (3-(4, 5-dimethylthiazoil-2-yl)-2,5-diphenyltetrazolium bromide) as an index, and represented as the ratio with respect to the number of cells without mitogen.

The amount of noradrenaline and dopamine excreted in urine from the second day to the third day of stress loading is shown in Table 5. As shown in Table 5, excretion of noradrenaline and dopamine in urine was significantly smaller in group (2) which was exposed to stress than in group (1) which were not exposed to stress. In group (3) which received the tripeptides, the decrease in excretion of noradrenaline and dopamine tended to be suppressed, compared to group (2) which received saline. It was thus recognized that IPP and VPP have a suppressive effect in stress induced decrease in excretion of noradrenaline and dopamine in urine.

TABLE 5

| Experimental Groups | Noradrenaline (mg/day) | Dopamine (mg/day) |
| --- | --- | --- |
| (1)no-stress, given saline | 0.296 | 0.466 |
| (2)stressed, given saline | 0.168* | 0.287* |
| (3)stressed, given VPP and IPP | 0.231*# | 0.396*# |

*significantly different from group (1) with significance level of 5%
significantly different from group (2) with significance level of 10%

Fischer ratio of serum amino acids after sacrifice is shown in Table 6. As shown in Table 6, Fischer ratio was significantly lower in group (2) which were exposed to stress than in group (1) which were not exposed to stress. On the other hand, Fischer ratio was significantly higher in group (3) which received the tripeptide than in group (2) which received saline.

TABLE 6

| Experimental Groups | Fischer Ratio |
| --- | --- |
| (1)no-stress, given saline | 3.34 |
| (2)stressed, given saline | 2.97* |
| (3)stressed, given VPP and IPP | 3.27# |

*significantly different from group (1) with significance level of 5%
significantly different from group (2) with significance level of 5%

Weight of thymus and spleen after sacrifice is shown in Table 7. The weight of thymus and spleen was lowered more in group (2) which were exposed to stress than in group (1) which were not exposed to stress. Weight of thymus and spleen tended to be slightly greater in group (3) which received the tripeptides, than in group (2) which received saline.

TABLE 7

| Experimental Groups | Thymus weight (mg) | Spleen weight (mg) |
| --- | --- | --- |
| (1)no-stress, given saline | 433 | 769 |
| (2)stressed, given saline | 202* | 453* |
| (3)stressed, given VPP and IPP | 226* | 495* |

*significantly different from group (1) with significance level of 5%

Mitogen reactivity of the spleen cells is shown in Table 8, and interleukin 2 productivity of the spleen cells is shown in Table 9. Decrease in mitogen reactivity and tendency toward decrease in interleukin 2 productivity were recognized in group (2) which were exposed to stress, compared to group (1) which were not exposed to stress. On the other hand, increase in mitogen reactivity and tendency toward increase in interleukin 2 productivity were recognized in group (3) which received the tripeptides, compared to group (2) which received saline.

TABLE 8

| | Mitogen Reactivity | |
| --- | --- | --- |
| Experimental Groups | ConA | PWM |
| (1)no-stress, given saline | 1.91 | 1.45 |
| (2)stressed, given saline | 1.56* | 1.26* |
| (3)stressed, given VPP and IPP | 1.80# | 1.37# |

*significantly different from group (1) with significance level of 5%
*significantly different from group (2) with significance level of 5%

TABLE 9

| Experimental Groups | Interleukin 2 Productivity (Unit/ml) |
| --- | --- |
| (1)no-stress, given saline | 6094 |
| (2)stressed, given saline | 4431 |
| (3)stressed, given VPP and IPP | 7086# | significantly different from group (2) with significance level of 10%

From these results, it is thus recognized that administration of IPP and VPP can suppress decrease in indices of immunological function caused by stress such as change in balance of blood amino acid (Fischer ratio), atrophy of thymus and spleen, and decrease in spleen cell reactivity.

What is claimed is:

1. A method of mitigating at least one symptom of stress in a mammal, wherein said symptom is selected from the group consisting of (a) reduction of noradrenaline production, (b) reduction of dopamine production, (c) reduction of interleukin-2 production (d) a decrease in the weight of the thymus and spleen, (e) a decrease in mitogen reactivity of spleen cells, and (f) a decrease in the Fischer ratio, said method comprising administering the tripeptide Ile-Pro-Pro or the tripeptide Val-Pro-Pro to a mammal which has been subjected to stress for a time and under conditions effective to increase noradrenaline production, increase dopamine production, increase interleukin-2 production, increase the weight of the thymus and spleen, increase the mitogen reactivity of spleen cells, or increase the Fischer ratio, wherein the Fischer ratio is the ratio of branched-alkyl to aromatic amino acids.

* * * * *